United States Patent
Davis et al.

[11] Patent Number: 5,192,206
[45] Date of Patent: Mar. 9, 1993

[54] DENTAL SYRINGE TIP AND ADAPTOR

[76] Inventors: Warren Davis, 3026 Sullivan Ave., Rosemead, Calif. 91770; David Wasserman, 2095 Mohigan Way, Las Vegas, Nev. 89109; Richard R. Mathews, 7950 S. Alameda St., Huntington Park, Calif. 90255

[21] Appl. No.: 596,987

[22] Filed: Oct. 11, 1990

Related U.S. Application Data

[63] Continuation-in-part of Ser. No. 351,431, May 12, 1989, Pat. No. 5,049,071, which is a continuation-in-part of Ser. No. 241,081, Sep. 6, 1988, abandoned.

[51] Int. Cl.⁵ .................................. A61C 17/00
[52] U.S. Cl. ............................. 433/80; 433/126
[58] Field of Search ............ 433/80, 126; 604/43, 604/45, 150, 264, 275, 283, 243, 241, 902, 905; 128/207.14

[56] References Cited

U.S. PATENT DOCUMENTS

| | | |
|---|---|---|
| 1,858,056 | 5/1932 | Pieper . |
| 2,460,473 | 2/1949 | Smith ................................. 128/349 |
| 2,560,915 | 7/1951 | Bamberger ......................... 128/350 |
| 2,641,839 | 6/1953 | Black ................................... 32/58 |
| 3,581,399 | 6/1971 | Dragan ................................ 32/60 |
| 3,593,423 | 7/1971 | Jones et al. ......................... 32/22 |
| 3,640,304 | 2/1972 | Fox et al. .......................... 433/80 |
| 3,727,310 | 4/1973 | Baker ................................... 32/22 |
| 3,771,527 | 11/1973 | Ruisi ................................ 128/350 |
| 3,874,083 | 4/1975 | Buckley ............................... 32/22 |
| 4,026,025 | 5/1977 | Hunt ................................... 32/22 |
| 4,248,589 | 2/1981 | Lewis .................................. 433/80 |
| 4,304,552 | 12/1981 | Wright et al. ..................... 433/126 |
| 4,531,913 | 7/1985 | Taguchi .............................. 433/80 |
| 4,619,612 | 10/1986 | Weber et al. ....................... 433/80 |
| 4,648,871 | 3/1987 | Jacob ................................. 604/149 |
| 4,834,653 | 5/1989 | Edwardson ....................... 433/118 |
| 4,975,054 | 12/1990 | Esrock .............................. 433/126 |

FOREIGN PATENT DOCUMENTS

| | | | |
|---|---|---|---|
| 1416921 | 10/1968 | Fed. Rep. of Germany | 433/80 |
| 1283435 | 11/1968 | Fed. Rep. of Germany | 32/22 |
| 3526579 | 7/1986 | Fed. Rep. of Germany | 32/33 |

OTHER PUBLICATIONS

Adec brochure, Autoclavable Syringe Tip Kits, 1 page.

Primary Examiner—Gene Mancene
Assistant Examiner—Nicholas D. Lucchesi
Attorney, Agent, or Firm—John Edward Roethel

[57] ABSTRACT

Various adaptors are used for securing a replaceable syringe tip in operative relationship to a handpiece body. The syringe tip is mounted on a tapered male connector set in the hollow interior of the adaptor. O ring seals and a metal flange member are used to prevent the leakage of air or water passing from the handpiece into the interior of the adaptor and then into the syringe tip. A captivated thumb nut is utilized to prevent the thumb nut from accidently disengaging completely from the adaptor. When the thumb nut is loosened to replace a syringe tip, the thumb nut will remain captivated on the adapter, only loosening enough to allow removal and insertion of a syringe tip.

32 Claims, 8 Drawing Sheets

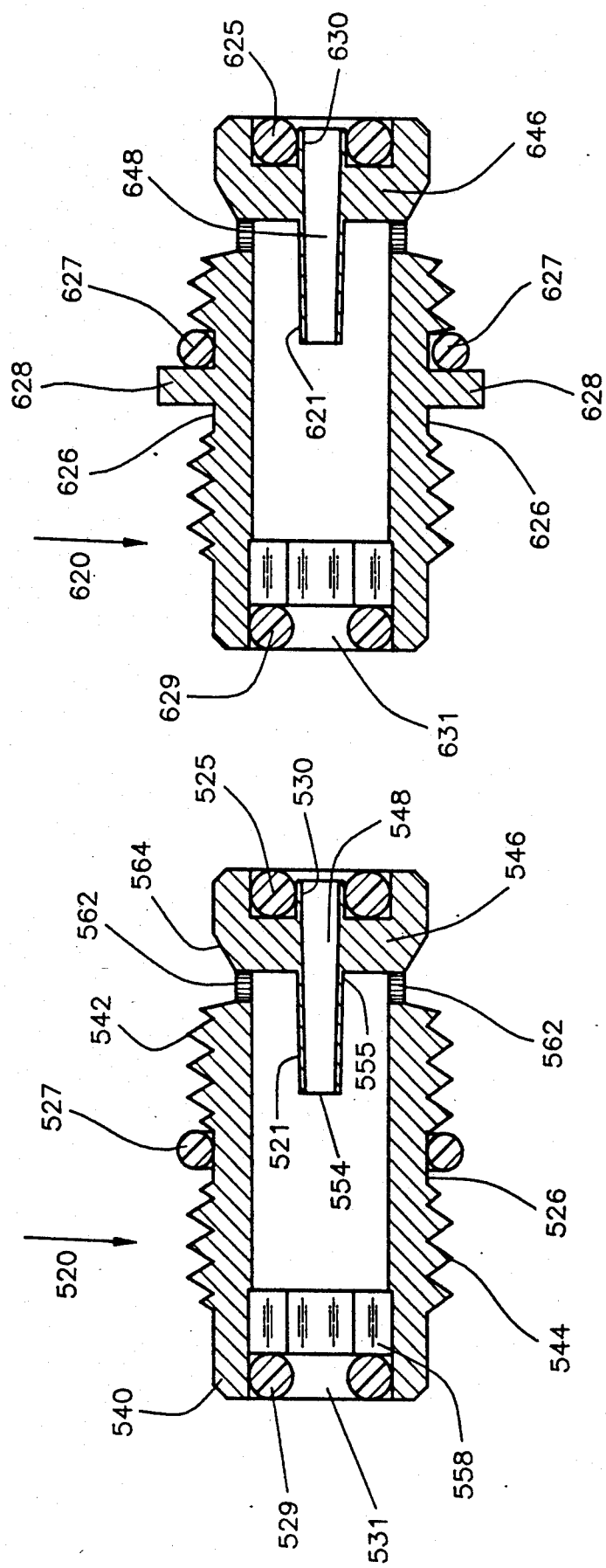

DENTAL SYRINGE TIP AND ADAPTOR

CROSS REFERENCE TO RELATED APPLICATION

This application is a Continuation-in-Part of Application Ser. No. 07/351,431, filed May 12, 1989, now U.S. Pat. No. 5,049,071 entitled "Dental Syringe Tip and Adaptor", which in turn is a Continuation-in-Part of application Ser. No. 07/241,081, filed Sep. 6, 1988, now abandoned, entitled "Dental Syringe Tip and Adaptor".

BACKGROUND OF THE INVENTION

This invention relates to dental syringe tip assemblies, and more particularly to dental syringe tip assemblies having a disposable tip, an innovative adaptor and a captivated thumb nut.

For the past twenty-five years, dentists have been using a three-way syringe. An air tube and a water tube join together at the handpiece. Two operating buttons are provided on the handpiece body to allow activation by the dentist of the air or water. By depressing the air button, air flows out of the tip into the appropriate area of the patient's mouth to dry the field of operation. By depressing the water button, a passive flow of water is emitted to clean and float away debris and congestion from the field of operation. By depressing both buttons simultaneously, a spray of air and water is emitted which flushes away debris which can then be vacuumed from the oral cavity. Typical of a three-way syringe assembly is that shown in U.S. Pat. No. 3,874,083 to Buckley.

During these twenty-five years, there has only been one significant improvement made to this essential piece of dental equipment. In approximately 1979, the tip of the syringe was made removable to allow for sterilization. Before 1979, tips were disinfected and cleaned by simply wiping them with alcohol. With the development of the removable tip, sterilization of each tip could be accomplished through the use of steam or chemical heat procedures. However, if done with the appropriate frequency, the tip becomes clogged and unusable in several months. This is due to minerals and other impurities in the steam used in an autoclave which causes alkaline and calcium deposits to build up in the orifices of the tip which interrupt the flow of air and water from the tip. The air and water orifices in the tip are quite small, so that any irregularities occurring during fabrication will also decrease the life expectancy of the tip. Any plugging of the tip orifices results in both a loss of spray pressure as well as a loss of spray accuracy. Tips are conventionally made out of metal and it would be cost prohibitive to discard a metal tip after only a single use.

With the rising incidence of communicable diseases such as hepatitis and acquired immune deficiency syndrome, extreme care must be taken to prevent the transmission of germs (viral or bacteria) from one patient to the next. With the conventional metal tips, it is necessary to sterilize the tip after each patient use. This is due to a condition that occurs in the end of the tip during use known as water retraction (also called suck-back or draw-back), which is a negative pressure applied to the water line. In a syringe, water retraction is used to prevent siphoning or dripping from the water line. When water retraction occurs, water, saliva and blood from the patient's mouth can be drawn back into the end of the tip and then passed on to the next patient. This provides the opportunity for the transfer of infection from one patient to the next. Also, latent bacterial growth can be promoted in both the tip and the entire water system lines because of the existence of this potentially contaminating material. Both the Center for Disease Control and the American Dental Association recommend that water lines be non-retracting. To further mitigate this possibility of cross-contamination from one patient to the next, the routine sterilization of handpieces as well as air/water syringes is desirable. In the case of handpieces and air/water syringes that cannot be sterilized, it is recommended that other complete cleaning and disinfection procedures be followed.

A disposable syringe tip is disclosed in U.S. Pat. No. 4,026,025 to Roderick S. Hunt. The plastic tip is disclosed as flexible and can be easily bent by hand without any special tools or heating. Such a flexible tip would suffer from the limitation that it would not function as a retractor. It is necessary when applying air, water or a spray to the patient's mouth to be able to use the syringe tip as a retractor to move the patient's tongue, cheeks or lips. If the syringe tip were flexible, it would fail to perform this important retraction function.

The syringe tip and mounting collet disclosed in the Hunt patent also have further design limitations. The chamfered surface on the end of the syringe tip effectively directs the air away from the water thereby impeding the formation of the water spray which is so important in a three-way syringe. The small circular air passages further limit the amount of air exiting the end of the tip and these air passages would be subject to being crimped closed when the flexible tip is bent. The syringe tip is press fit on the end of a small nipple on the collet in such a manner that the air and water pressure leaving the handpiece body and entering the syringe tip would lead to a loosening of the press fit thereby causing the syringe tip to dislodge from the nipple. This design is also not adaptable to most three-way piece syringe assemblies on the market.

It is an object of the present invention to alleviate the transmission of germs (viral or bacteria) which cause infection or disease, from one patient to the next, and to eliminate the need to resterilize a syringe tip after each use.

It is a feature of the present invention to provide a clear, plastic disposable rigid syringe tip that is discarded after its use on a single patient, as well as to provide a novel adaptor to connect the disposable syringe tip to the handpiece body.

It is an advantage of the present invention that a more sterile dental environment will be created as well as the flow of air, water or spray from the syringe to the oral cavity will be improved.

It is a further object of the present invention to provide novel adaptors for connecting syringe tips to the handpiece body and improving the flow and distribution of air and water into the patient's mouth.

It is a further feature of the present invention to provide adaptors being specially designed to receive various sealing rings and also adaptors provided with improved passageway configurations.

It is a further advantage of the present invention that the particular adaptors utilized prevent water and air leakage as well as improving the flow of water and air from the handpiece body through the adaptor and the syringe tip and into the patient's mouth.

It is a further object of the present invention to provide for an easy and simple connection and disconnection of the syringe tip from the adaptor while at the same time minimizing the possibility that the locking thumb nut securing the syringe tip to the adapter will become lost or misplaced.

It is a further feature of the present invention to provide a captivated locking thumb nut assembly that prevents the locking thumb nut from becoming disengaged from the adaptor unless the locking thumb nut is oriented into a position in which disengagement is possible.

It is a further advantage of the present invention that a used syringe tip can be removed and replaced with a new syringe tip by merely loosening the captivated locking thumb nut and thus the locking thumb nut cannot become accidently separated from the adaptor, thus minimizing the loss or misplacement of the captivated locking thumb nut.

Other objects, features and advantages will become apparent when the detailed description and drawings of the present invention are considered.

BRIEF DESCRIPTION OF THE DRAWINGS

FIG. 15 shows in cross-section an alternate embodiment of the adaptor of the present invention.

FIG. 16 shows in cross-section another alternate embodiment of the adaptor of the present invention.

DETAILED DESCRIPTION OF THE PREFERRED EMBODIMENTS

Figure 1:
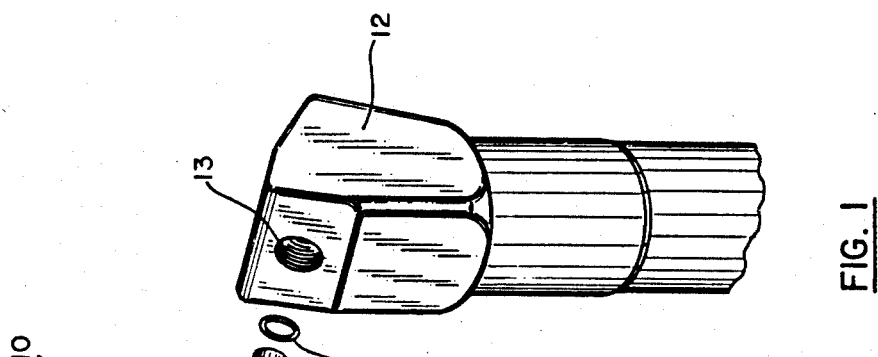
FIG. 1 shows an exploded view of a dental syringe assembly incorporating the present invention.

A dental syringe assembly 10 includes a conventional handpiece body 12 on which is mounted a syringe tip 14. The tip 14 is an elongated cylindrical member preferably made of a rigid plastic material. The tip 14 is provided with a bend 17, at preferably an angle of approximately 30°, to provide easy access to any portion of the patient's mouth during use of the syringe assembly. An adaptor 20 screws into a threaded opening 13 in the handpiece body 12 and is sealed toward one end of the adaptor by a first rubber O-ring 16. A second rubber O-ring 22 provides a seal at the midpoint of the adaptor 20.

The tip 14 is press fit onto a tapered male connector 21 (see FIGS. 7 and 8) that is mounted axially in the interior of the adaptor 20. A collet 26 and a third O-ring 24 provide a seal for the tip 14—male connector 21 assembly. A nut 28 comprises a locking assembly and screws onto the threads 44 on the outer surface of adaptor 20 to secure the tip 14, collet 26 and third O ring 24 in place. Each of these parts, other than the specific tip 14 and the specific adaptor 20, are the conventional assembly for a three-way syringe tip assembly such as Model No. 23-0090-00 or Model No. 90-0125-00 sold by the Adec Corporation of Newberg, Oreg. or the DCI 3-way syringe sold by Air-Con Inc. of Portland, Oreg.

The tip 14 is shown in detail in FIGS. 2 through 6. The tip 14 is designed to be disposable after a single use. The tip material is fabricated in a single-step extrusion process, and is made from any rigid transparent plastic. A rigid plastic is preferred to fulfill the need to use the tip for continued retraction of the cheek and tongue by the dental operator. In a preferred embodiment, the tip 14 is made from a polycarbonate plastic or other rigid plastic materials. Suitable rigid plastic transparent material is that sold by General Electric Co. under the trademark Ultem 1000 or that sold by Victrex Corp. under the trademark Peek. Other plastics that have been found to be suitable for use in the syringe tip of the present invention are nylon and Lexan ®.

As shown in FIGS. 2 through 6, a central water passageway 32 runs the entire length of the tip 14 and is used to deliver water from the handpiece body 12 to the patient's mouth. Three air passageways 34 also run the entire length of the tip 14, are disposed circumferentially about the central passageway 32 and are used to deliver air from the handpiece body 12 to the patient's mouth. If both air and water are delivered through the tip 14 simultaneously, a spray results at the exit end 15 of the tip 14.

In a preferred embodiment, the elongated cylindrical member comprising tip 14 has a diameter in a range generally of 0.140"–0.150", and most preferably has a diameter of approximately 0.145". The water passageway 32 has a diameter in a range of generally 0.035"–0.039", and most preferably has a diameter of approximately 0.036". Each air passageway 34 comprises in cross section an arcuate section (see FIG. 3) approximately one-third of the circumference of the tip 14. Each arcuate section has a width in a range of generally 0.16"–0.20", and preferably has a width of approximately 0.017". The arcuate sections are separated from one another by thin support segments 38, each having a thickness of approximately 0.018".

The combined cross-sectional area of the three arcuate sections comprising the air passageways 34 is approximately 0.0039". The air passageways 34 thereof encompass approximately 80% of the combined area of the three air passageways 34 plus the three support segments 38. In other words, the combined cross-sections of the air passageways 34 are approximately 80% of the maximum cross-section if the second passageway were a continuous annulus.

In a conventional three way syringe, the water pressure is generally on the order of 35 psi and the air pressure is generally on the order of between 60 psi and 80 psi. The configuration of the syringe tip 14 shown in FIG. 3 produces a low air pressure at the exit end 15 of the syringe tip and thus low aerosol spray (when both the air and water are activated) due to the air passageways 34 comprising approximately 80% of the maximum opening that could be achieved by using a continuous annulus for the air passageway.

If excessive aerosol is used, the possibility exists that the work area will be contaminated with airborne pathogens thus endangering both the dentist and other persons present in the work area. For example in the Hunt patent (U.S. Pat. No. 4,026,025), the air passageways are quite small in size, thus resulting in a high air pressure when the air impacts the water at the end of the syringe tip. This results in a spray having very high aerosol. The risk of airborne pathogens from the use of the syringe tip disclosed in the Hunt patent is quite probable.

Figure 3:
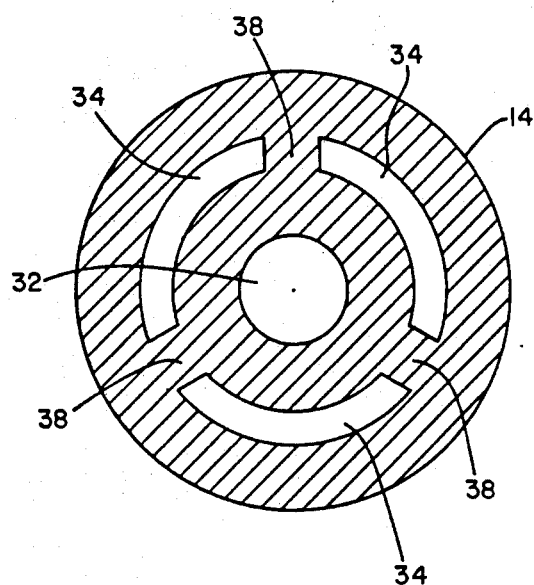
FIG. 3 shows a cross-section taken along line 3—3 of FIG. 2 of the disposable syringe tip of the present invention.

While the air passages 34 shown in FIG. 3 are shown in cross-section as an arcuate section, other cross-sectional shapes can also be used such as rectangular sections, triangular sections and elliptical sections Likewise, the central water passageway 32, shown in FIG. 3 as having a circular cross-section, can alternatively have other cross-sections such as square, rectangular, elliptical or triangular.

The support segments 38 are also shown in FIG. 3 as being symmetrically oriented about the circumference of the tip 14 approximately 120°±4° apart. It is also possible to asymmetrically orient the support segments 38 about the circumference of the tip which would result in some of the air passages 34 being longer in cross-section than others. Also, while three support segments 38 are shown, as few as two or as many as four or more support segments can also be used.

Figure 4:
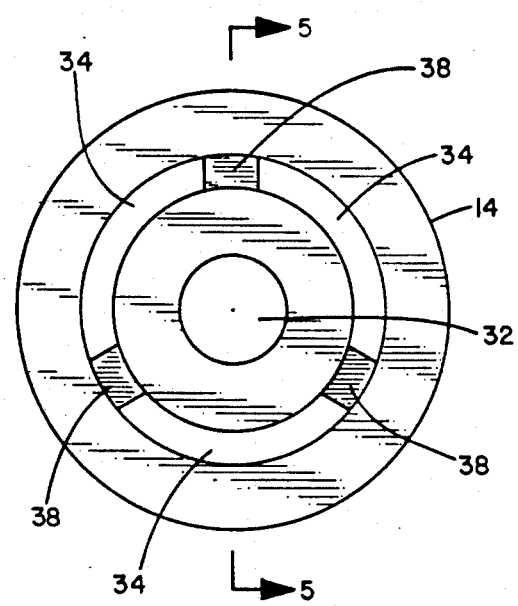
FIG. 4 shows an end view taken along line 4—4 of FIG. 2 of the exit end of the disposable syringe tip of the present invention.
Figure 5:
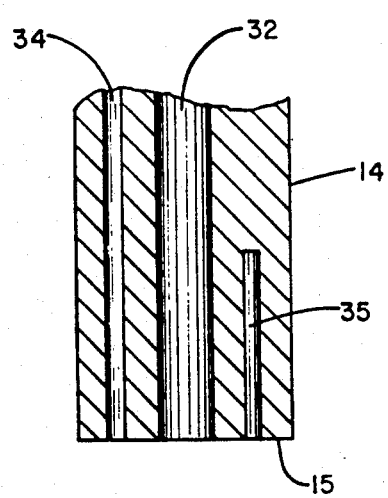
FIG. 5 shows a cross-section of the exit end of the disposable syringe tip taken along line 5—5 of FIG. 4.
Figure 6:
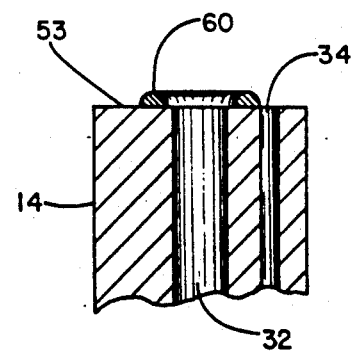
FIG. 6 shows an end view of the entrance end of the disposable syringe tip taken along line 6—6 of FIG. 2.

As shown in FIGS. 4 and 5, at the exit end 15 of the tip 14, the air passages 34 combine to form a continuous 360° annulus 35 around the water passage 32. This can be achieved during the fabrication of the tip 14 by die-cutting to the desired depth each support segment 38 inward from the exit end 15 of the tip 14. While die-cutting is the preferred way of forming the continuous annulus 35, other methods can be used to remove the support segments 38 to the desired depth. In the preferred embodiment, the depth of the continuous annulus 35 from the exit end 15 of the tip 14 inward is approximately 0.125".

The continuous annulus 35 achieves a quite effective mixing of the air and water which results in a uniform spray which is easily directed by the dental operator at the needed locations in the patient's mouth.

Figure 7:
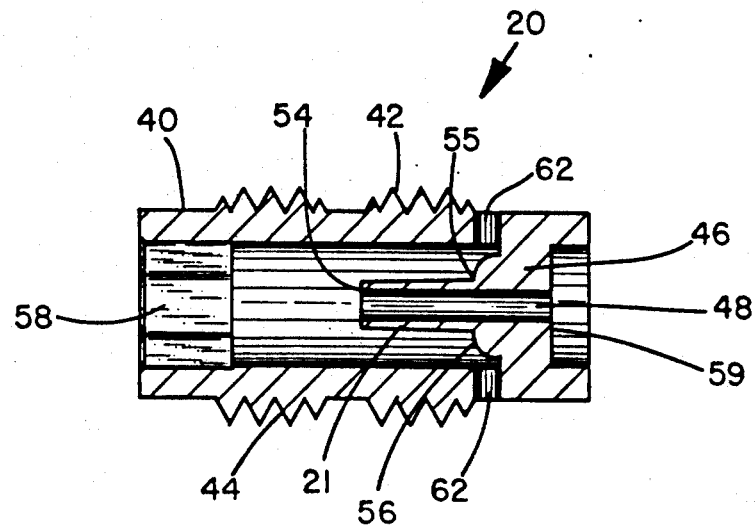
FIG. 7 shows in section the adaptor of the present invention.
Figure 8:
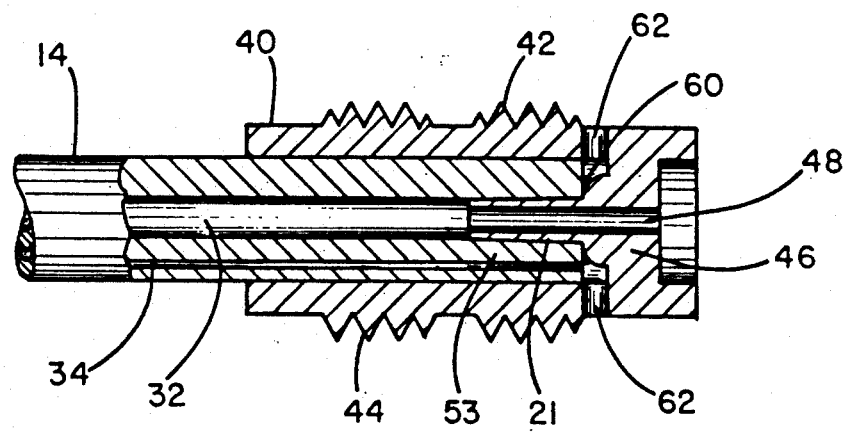
FIG. 8 shows the adaptor with a portion of the syringe tip mounted thereon.

FIGS. 7 and 8 show the adaptor 20 that is used to connect the tip 14 to the handpiece body 12. The adaptor 20, preferably made of metal, comprises a generally cylindrical body having a hollow interior. The exterior wall 40 of the adaptor 20 has a first set of threads 42 for attaching the adaptor 20 to the threaded opening 13 in the handpiece body 12. A baffle 46 extends across the hollow interior of the cylindrical adaptor 20. Formed integrally with the baffle 46 is a male connector 21 formed as a cylindrical member and having an axial opening 48 therethrough. The male connector 21 is tapered to receive the entrance end 53 of the tip 14. The male connector 21 is also formed of metal and has an outer diameter at its forward end 54 of approximately 0.032" and tapers out at its bottom end 55 to a diameter of approximately 0.038". The male connector 21 is press fit into the water passageway 32 of the end 53 of the tip 14. A rounded shoulder 56, which surrounds the bottom of the male connector 21 at the location where the male connector 21 joins the baffle 46, cooperates with a resilient O-ring coating 60 on the entrance end 53 of the tip 14 (see FIG. 6) to form a seal to prevent water from leaking. The baffle 46 communicates at 59 through axial opening 48 with a water line by way of a valve (not shown) in the handpiece body 12.

A plurality of circumferentially arranged channels 62 in the cylindrical body provide openings to allow the air from the handpiece body 12 to pass to the hollow interior of the adaptor 20 and then into the air passageways 34.

A second set of threads 44 is provided on the exterior wall 40 of the adaptor 20. These threads 44 cooperate with the threads in nut 28 to seal the tip 14 to the adaptor 20.

The forward interior portion of the adaptor 20 is provided with an hexagonal cross-section 58 which allows the use of an allen wrench to screw the adaptor 20 into the opening 13 in the handpiece body 12.

The present invention yields significant advantages over the syringe tip-adaptor assemblies used previously. By using a disposable syringe tip, a source of infection and cross-contamination of micro-organisms from one patient to the next is eliminated. When a three-way syringe is used, back pressure is created at the end 15 of the syringe tip 14 whenever the air and water flow is abruptly cut off. This back pressure can cause contaminated water, saliva or blood to be drawn back into the tip openings. If the tip 14 were to be used on a second patient, any micro-organisms in the contaminated water, saliva or blood from the first patient could infect the second patient. A disposable tip 14 used for each patient eliminates this problem.

Existing metal tips should be sterilized prior to use using an autoclave sterilization system. The disposable tip eliminates the need for this autoclave sterilization equipment. Each tip 14 is sanitary during the manufacturing process and is then packaged. A dentist selects a packaged tip, removes the tip from its package or visually inspects the tip if it is already installed. The clear rigid plastic material from which the tip is made allows visual verification of the tip's sanitary state. If sterilization is required, such can be achieved during the manufacturing process by using any suitable sterilization process, such as gamma ray sterilization.

The prior art metal tip comprised two concentric tubes—an inner water tube surrounded by an outer air tube. In practice, the orifice at the end of the prior art metal tip can be quite irregular causing uneven spray when the air and water flows are effected simultaneously. Uneven flows results in an unpredictable spray pattern.

The extruded tip 14 of the present invention yields very uniform orifices for both air and water at the end 15 of the tip 14. This results in a uniform distribution of air, water or spray. A continuous, uninterrupted air supply through parallel air passageways 34 mitigates air turbulence and therefore produces a more accurate and controlled spray.

The adaptor 20 is different from the prior art adaptors. The tapered male connector 21 with the axial opening 48 provides a mounting location for the tip 14 and keeps the water supply separate from the air supply until they are mixed together at the end 15 of the tip 14 to form the spray. When the air and water are activated simultaneously by the dental operator, the continuous 360° air annulus 35 around the central water passage 32 combines to produce a fine spray.

Figure 9:
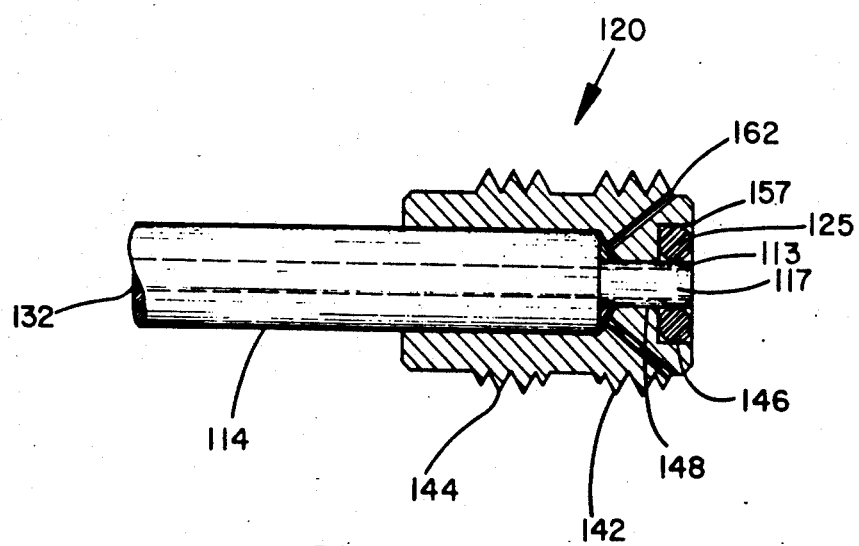
FIG. 9 shows in partial cross-section an alternate embodiment of the syringe tip and adaptor of the present invention.

An alternate embodiment of the present invention is shown in FIG. 9. The adaptor 120 is a conventional adaptor used in a conventional all-metal dental syringe assembly. The adaptor 120 has a first set of threads 142 for attaching the adaptor 120 to the threaded opening 13 in the handpiece body 12 (FIG. 1). The adaptor 120 has a second set of threads 144 which cooperate with the threads in nut 28 (FIG. 1) to seal the tip 114 to the adaptor 120. A plurality of circumferentially-disposed channels 162 (only one shown) are provided in the body of the adaptor 120 to allow air from the handpiece body 12 to pass to the hollow interior of the tip 114.

Figure 2:
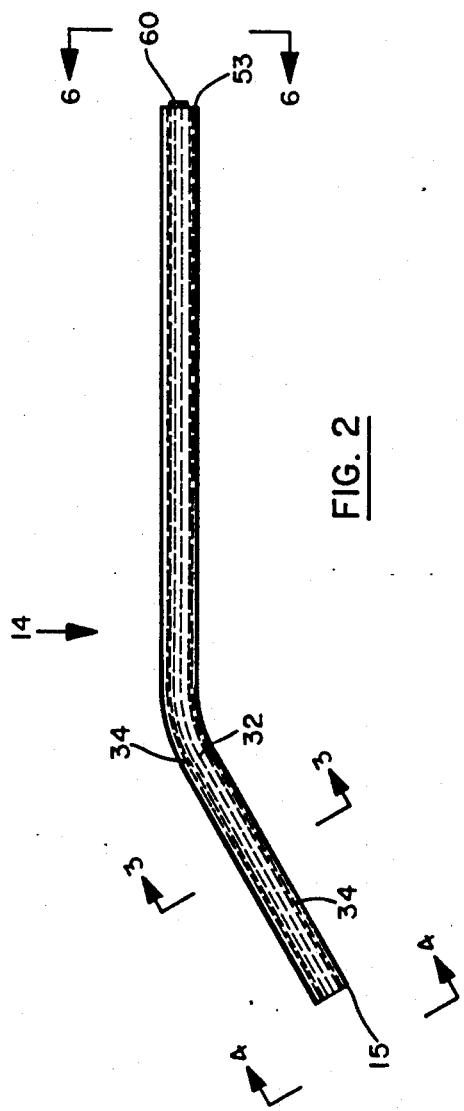
FIG. 2 shows a disposable syringe tip of the present invention.

The syringe tip 114 is similar to the tip 14 shown in FIGS. 2-4. The tip is fabricated from rigid plastic material and has the same internal cross-section configuration shown in FIGS. 3 and 4. The tip 114 has a tip extension 113 formed integrally with the tip 114 at the entrance end of the tip 114. The tip extension 113 extends through an axial opening 148 in a baffle 146 that extends across the interior of the adaptor 120. The adaptor 120 at its end 157 has an insert portion to accommodate an annular rubber sealing ring that surrounds that tip extension 113.

In the preferred embodiment, the outer diameter of the tip extension 113 is in the range generally of 0.062"-0.066", and most preferably is approximately 0.064". The length of the tip extension 113 is in the range generally of 0.012"-0.032", and most preferably has a length of approximately 0.022".

The tip extension 113 has a hollow central channel 117 that allows water from the handpiece body 12 to pass into the central passageway 32 of the tip 114.

Figure 10:
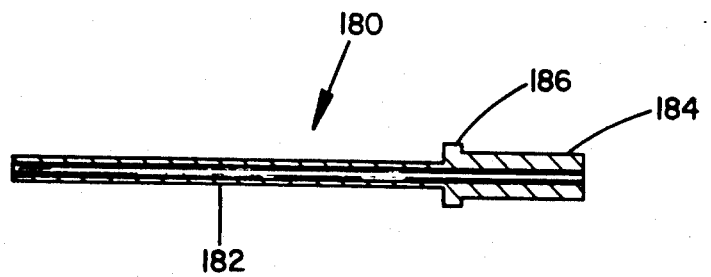
FIG. 10 shows in cross-section a coupling device used in an alternate embodiment of the present invention.

FIG. 10 shows in cross-section a coupling device 180 used in connection with an alternate embodiment of the present invention. The coupling device 180 comprises a mounting stem 184 having an expanded shoulder 186 and an interior hollow member 182.

Figure 11:
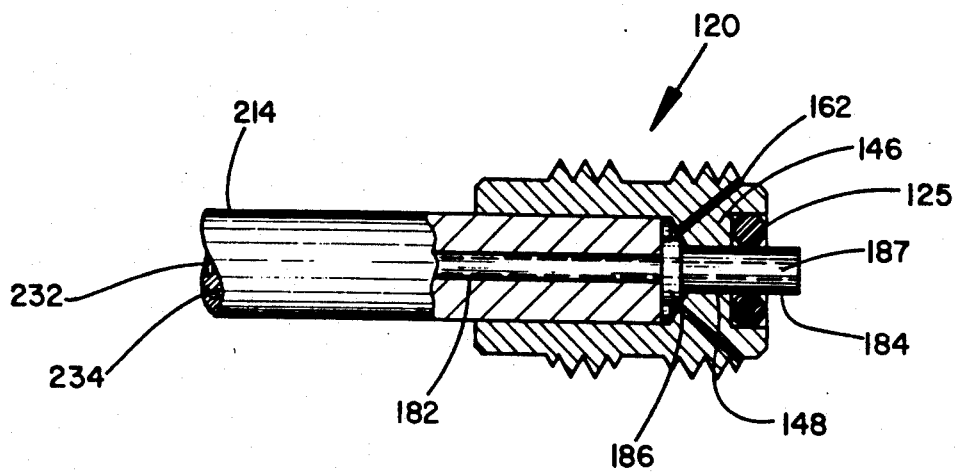
FIG. 11 shows in partial cross-section the syringe tip-coupling device-adaptor assembly of an alternate embodiment of the present invention.

The coupling device 180 in use is shown in FIG. 11. A conventional adaptor 120 (having the same elements as described with reference to FIG. 9) has a coupling device 180 mounted therein. The mounting stem 184 of the coupling device 180 is positioned in the axial opening 148 of the baffle 146 and is held in place by an annular rubber sealing ring 125. The expanded shoulder 186 of the coupling device 180 fits against the interior wall of the baffle 146. A plastic syringe tip 214 is press fit onto the interior hollow member 182 of the coupling device 180 Water from a handpiece body 12 is directed down the hollow passageway 187 in the coupling device 180 to the central passageway 232 of the tip 21. The expanded shoulder 186 does not block the air passageway 162 that provides air to the air passageways 234 in the tip 214.

In the preferred embodiment, the overall length of the coupling device 180 is in the range of generally 0.815"-0.835", and most preferably has a length of approximately 0.825". The coupling device 180 has a mounting stem 184 that has a length in the range of generally 0.165"-0.185", the expanded shoulder 186 has a length in the range generally of 0.020"-0.030" and the hollow tip member 182 has a length in the range generally of 0.615"-0.635". In the most preferred embodiment, the mounting stem has a length of approximately 0.025" and the hollow tip member has a length of approximately 0.625".

Other advantages inure from the use of plastic as the material from which the tip 14 is fabricated. A plastic tip will transmit less heat and cold to sensitive tissues in the oral cavity. Plastic tips are not electrically conductive and will not transmit a spark which can occur during modern dental treatments using electro-surgical devices. Also plastic tips are not harmed by the presence of ultrasonic devices.

The tip 14 is fabricated from a good quality, rigid plastic. The bend 17 in the tip 14 is provided during a heat forming step and once the plastic has cooled, the bend is a permanent part of the rigid tip 14. The entire tip fabrication process including extruding the plastic with the central water passage 32 and the arcuate section air passages 34, cutting the plastic extrusion to length, heat forming the bend 17, die-cutting the continuous 360° air annulus 35 and forming the resilient O-ring seal 60 is performed in a special multiple operation machine.

Figure 12:
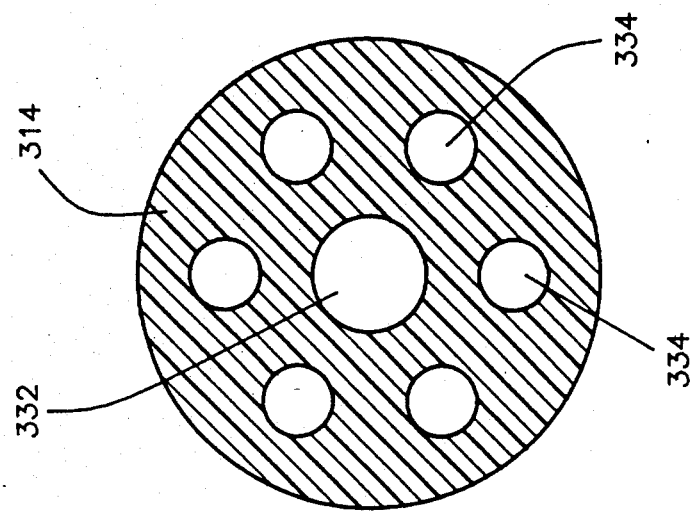
FIG. 12 shows a cross-section of an alternate embodiment of the disposable syringe tip of the present invention.

FIG. 12 shows in cross-section another embodiment of the syringe tip 314 of the present invention. This alternate embodiment utilizes a plurality of circular cross-sectioned air passageways 334 surrounding the circular cross-sectioned central water passageway 332. The circular air passageways 334 are generally uniformly spaced around the circumference of the central water passageway 332. In the preferred embodiment, six air passageways 334 are disposed generally 60° apart around the central water passageway 332.

In a typical construction of this embodiment, the central water passageway 332 has a diameter in a range of generally 0.035"-0.039", and most preferably has a diameter of approximately 0.036". Each air passageway 334 has a diameter in a range of generally 0.021"-0.024", and most preferably has a diameter of approximately 0.022". The overall diameter of the syringe tip 314 is between 0.141" and 0.149", and most preferably has an overall diameter of 0.145". The center of the central water passageway 332 is preferably within 0.002" of the center of the syringe tip 314.

Based on these specifications for the syringe tip 314, the central water passageway 332 and the six air passageways 334 shown in FIG. 12, the air passageways 334 effect approximately a 36% opening as compared to the approximately 80% opening of the syringe tip shown in FIG. 3. The smaller total air opening results in greater air pressure and a greater aerosol at the exit end of the syringe tip. The greater air pressure gives the dentist more power to clean the treated area in the patient's mouth, yet the aerosol level is not so high as to risk airborne pathogens.

In the preferred embodiments of the present invention, the combined cross-sectional areas of the air passageway openings should be at least approximately 30% of the total cross-sectional area that would result if the air passageways were formed as a single continuous annulus completely surrounding the central water passageway. This lower limit on the percentage of the opening is to minimize the amount of the aerosol. If the combined air passageway openings exceed approximately 85%, then the air pressure becomes too low to effectively clean the treatment area of the patient's mouth.

The syringe tip is preferably made from clear nylon or clear Lexan® and must be able to be formed into a fixed bend of 30° to allow the dentist to use the end of the syringe tip as a retractor in the patient's mouth.

Figure 13:
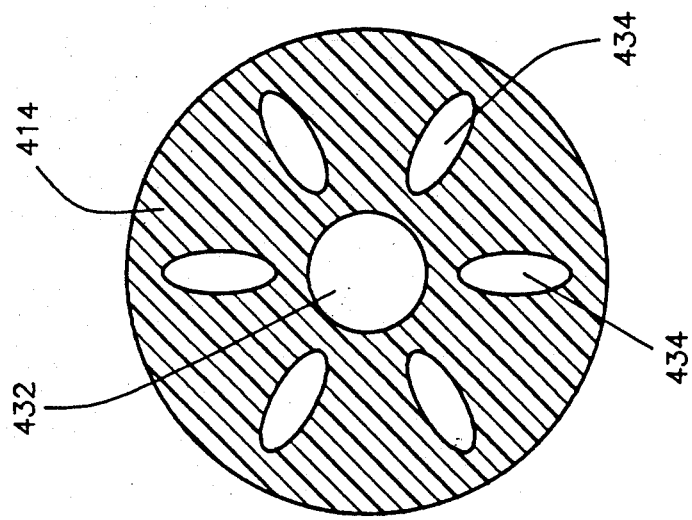
FIG. 13 shows a cross-section of another alternate embodiment of the disposable syringe tip of the present invention.

FIG. 13 shows another alternate embodiment of the syringe tip of the present invention. This syringe tip 414 is constructed similar to the syringe tip shown in FIG. 12 having a generally circular central water passageway 432, but the air passageways 434 are radially elliptical in shape.

Figure 14:
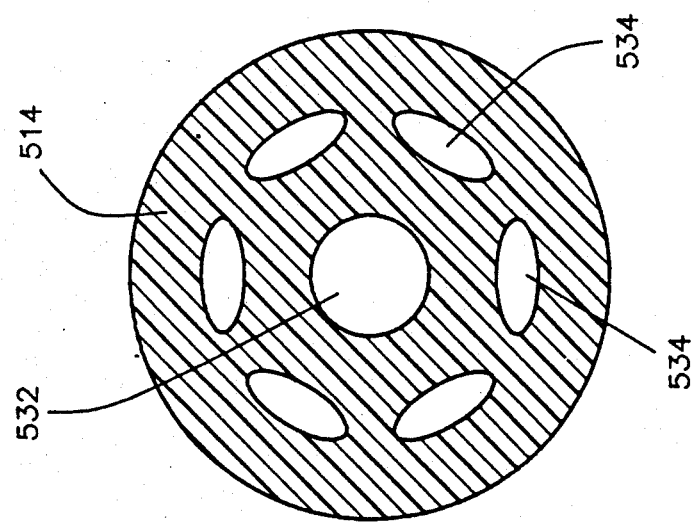
FIG. 14 shows a cross-section of yet another alternate embodiment of the disposable syringe tip of the present invention.

FIG. 14 shows another alternate embodiment of the syringe tip of the present invention. This syringe tip 514 is constructed similar to the syringe tip shown in FIG. 13 having a generally circular central water passageway 532, but the air passageways 534 are tangentially elliptical in shape.

By utilizing a multiplicity of air passageways around the central water passageway (as shown in FIGS. 12, 13 and 14), the syringe tip can be fabricated with a more circular central water passageway. The more air passageways around the central passageway, the better the fit of the syringe tip to the tapered mounting stem on the interior of the adaptor.

FIG. 15 shows another alternate embodiment of the adaptor 520 that is used to connect the syringe tip to the handpiece body. The adaptor 520, preferably made of metal, comprises a generally cylindrical body having a hollow interior. The exterior wall 540 of the adaptor 520 has a first set of threads 542 for attaching the adaptor 52 to the threaded opening in the handpiece body. A baffle 546 extends across the hollow interior of the cylindrical adaptor 520.

Formed integrally with the baffle 546 is a male connector 521 formed as a cylindrical member and having an axial opening 548 which extends through the male connector 521 and the baffle 546. This axial opening 548 is the passageway for feeding water from the handpiece to the central water passageway in the syringe tip.

The male connector 521 is tapered to receive the entrance end of the syringe tip. The male connector 521 is also preferably formed of metal and has an outer diameter at its forward end 554 of approximately 0.032" and tapers out at its bottom end 555 to a diameter of approximately 0.038". The central water passageway of the entrance end of the syringe tip is press fit onto the male connector 521. The length of the male connector 521 is selected to be long enough so that the syringe tip can be press fit onto the male connector 521 without cracking the syringe tip. This design provides a more secure water tight seal that requires less push and twist of the syringe tip when it is being mounted on the male connector 521.

Because the male connector 521 tapers from an outer diameter of approximately 0.032" to an outer diameter of approximately 0.038", if the male connector 521 is too short, the taper will be too rapid and the plastic syringe tip will have a tendency to crack instead of stretch as the syringe tip is press fit over the male connector 521.

In the preferred embodiment, a circumferentially arranged channel 562 (and in the most preferred embodiment, at least two channels 562) in the body of the adaptor provide an opening to allow the air from the handpiece body to pass into the hollow interior of the adaptor 520 and then into the air passageways in the syringe tip. Each channel 562 is made by providing a chamfered cut 564 into the outer surface of the body of the adapter 520. The chamfered surface 564 provides a more positive air flow from the handpiece into the channel 562.

A second set of threads 544 is provided o the exterior wall 540 of the adaptor 520. These threads 544 cooperate with the threads in the locking thumb nut to seal the syringe tip to the adaptor 520. The forward interior portion of the adaptor 520 is provided with an hexagonal cross-section 558 which allows the use of an allen wrench to screw the adaptor 520 into the opening in the handpiece body.

A first O ring seal 525 is provided at the handpiece connection end of the adaptor 520 to prevent leakage from the water passing from the handpiece into the interior of the adaptor. A mounting member 530 is machined or otherwise attached to the baffle 546 to securely hold the first O ring seal 525 on the adaptor 520. This mounting member 530 not only prevents the first O ring seal 525 from being pulled into the water passageway 548, but also alleviates any leakage of water passing from the handpiece to the interior of the adaptor 520 and then into the syringe tip.

A second O ring seal 527 is provided around the body of the adaptor 520 on a flat section 526 of the adaptor 520 between the first set of threads 542 and the second set of threads 544. This second O ring seal 527 prevents the leakage of air passing from the handpiece to the interior of the adaptor 520. A third O ring seal 529 is provided in a recess 531 at the thumb nut connection end of the adaptor 520 to secure the syringe tip inside the adaptor 620.

FIG. 16 shows yet another adaptor that can be used in the present invention. The adaptor 620 shown in FIG. 15 is similar to the adaptor 520 shown in FIG. 15 with the reference numerals referring to like parts in FIG. 16.

In order to more tightly seal the adaptor 620 into the handpiece and to prevent any leakage of air around the outside of the adaptor 620, a circumferential flange 628, having a height greater than the height of the second O ring seal 627, is machined or otherwise attached to the adaptor at the location of the flat section 626. When the adaptor is threaded into the handpiece, the second O ring 628 will deform against this flange 628 to solidly seal the adaptor into the handpiece and substantially prevent any leakage of air from the handpiece around the outside of the adaptor.

Another improvement provided for in the present invention is a captivated thumb nut. As shown in FIG. 1, the thumb nut 28 threads over the adaptor 20 and, by means of the collet 26 and the seal 26, securely holds the syringe tip 14 in the adaptor 20. When it is desired to replace the syringe tip 14, the thumb nut 28 is loosened and the syringe tip 14 can be slid out of the adaptor 20 and replace with another syringe tip 14.

One of the problems that occurs in dental offices is that the thumb nut 28 can disengage completely from the adaptor 20 and can become lost or misplaced. The captivated thumb nut of the present invention is designed to prevent the thumb nut 28 from accidently disengaging completely from the adaptor 20. When the thumb nut 28 is loosened to replace a syringe tip, the thumb nut 28 will remain captivated on the adapter 20 only loosening enough to allow removal and insertion of a syringe tip. Should it become necessary to completely remove the thumb nut 28 from the adaptor, the thumb nut can be oriented in a preferred position to allow complete disengagement of the thumb nut 28 from the adaptor 20.

Figure 17:
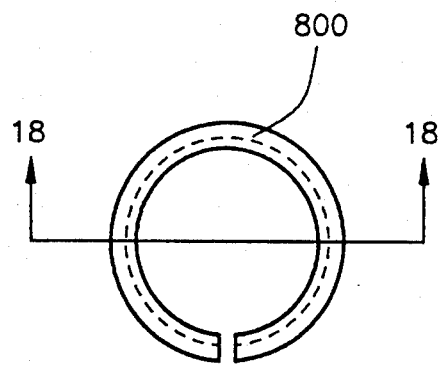
FIG. 17 shows a top view of the ring element used in the captivated locking thumb nut of the present invention.
Figure 18:
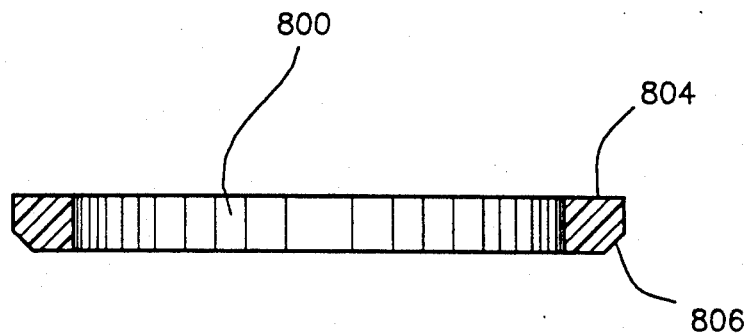
FIG. 18 shows is a sectional view taken along line 18—18 of FIG. 17 of the ring element used in the captivated locking thumb nut of the present invention.

The captivation of the thumb nut onto the adaptor is achieved by utilizing a captivating element within the overlock of the outside of the adaptor and the interior of the thumb nut. Referring to FIGS. 17 and 18, the captivating element 800 is a generally circular metal washer-like member with a small segment or portion of its circumference omitted. One side of the captivating element 800 is provided with a beveled edge 806 around its entire circumference. The other side of the captivating element 800 is provided with a flat edge 804 around its entire circumference.

Figure 19:
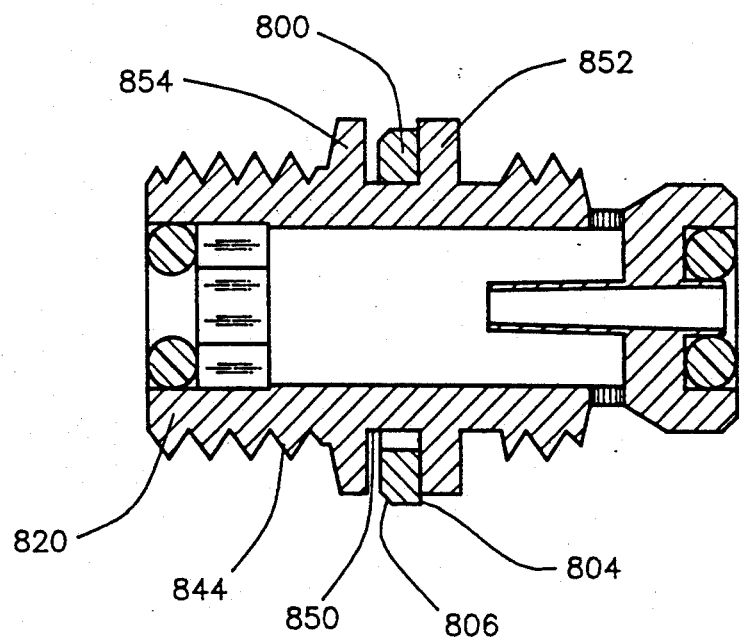
FIG. 19 shows in cross-section the captivated locking thumb nut of the present invention mounted on an adaptor.
Figure 20:
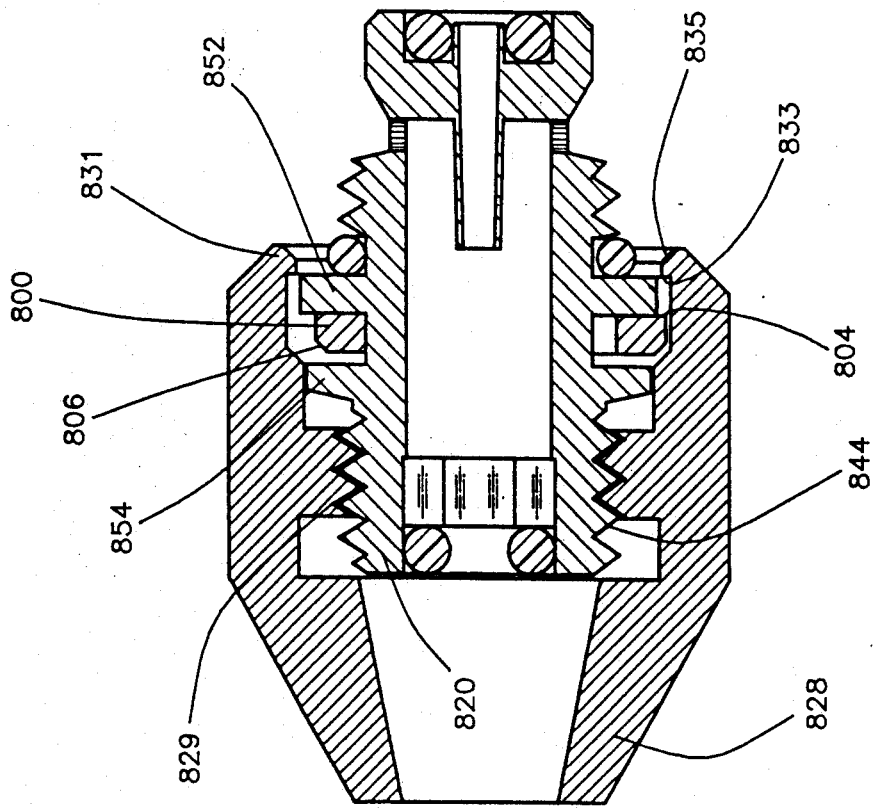
FIG. 20 shows in cross-section in a horizontal orientation the captivated locking thumb nut of the present invention mounted on an adaptor and surrounded by a locking thumb nut.

FIG. 19 shows the captivating element disposed around the adaptor 820. The captivating element 800 is mounted in a channel 850 at approximately the center of the adaptor 820. The channel is formed between a first circumferential flange 852 and a second circumferential flange 854 around the body of the adaptor 820. The internal diameter of the captivating element 800 is larger than the cross-section of the adaptor 820 at the location of the channel 850 so the captivating element 800 hangs loosely on the adaptor as shown in FIG. 19. When the adaptor 820 is disposed horizontally as shown in FIGS. 19 and 20, a portion of the adaptor hangs below the end of the first flange 852 and the second flange 854.

The thumb nut 828 is a generally hollow conically shaped member designed with a set of interior threads 829 which cooperate with the interior threads 844 on the adaptor. On end of the thumb nut 828 has a circumferential shoulder 832 with an interior flat edge 833 and an exterior beveled edge 835.

When it is desired to attach the thumb nut 828 to the adaptor 820, the interior threads 829 on the thumb nut 828 simply thread onto the exterior threads 844 of the adapter 820. As the threads 829 on the thumb nut 828 reach the captivating element 800, the beveled edge 835 on the shoulder 850 of the thumb nut 828 interacts with the beveled edge 806 on the captivating element. The advancing beveled edge 835 on the thumb nut 828 causes the captivating element 800 to orient itself and align itself with the diameter of the first flange 852 so that the thumb nut 828 can pass over captivating element 800. Once the thumb nut 828 has been screwed onto the adaptor 820, the captivating element 800 is no longer aligned by the beveled edge 835 on the thumb nut 828 and the captivating element 800 falls out of axial alignment with the adaptor 820 due to gravity (as shown in FIG. 20).

If disassembly of the thumb nut 828 from the adaptor 820 is attempted while the adaptor 820 is held in a non-vertical position, the flat edge 835 on the shoulder 850 of the thumb nut 828 will catch on the flat edge 804 of the captivating element 800. This will stop any further disassembly of the thumb nut 828 and hold the thumb nut 828 captivated on the adaptor 820. The thumb nut 828 will be loosened enough to permit replacement of a syringe tip, but the thumb nut 828 being captivated by the captivating element 800 on the adaptor 820 prevents loss or misplacement of the thumb nut 828.

Figure 21:
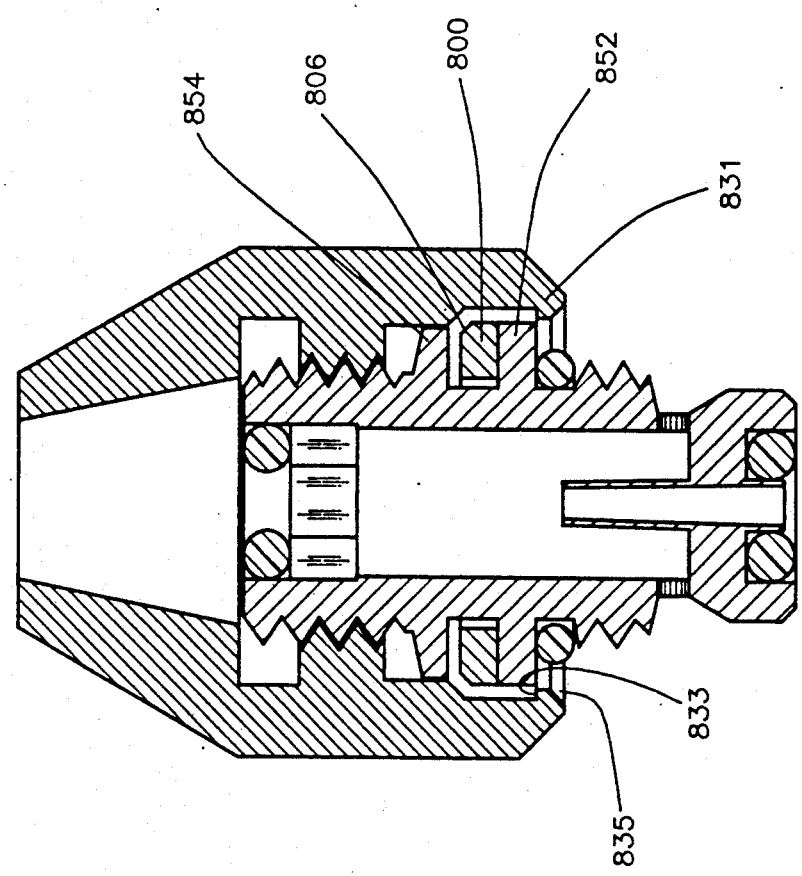
FIG. 21 shows in cross-section in a vertical orientation the captivated locking thumb nut of the present invention mounted on an adaptor and surrounded by a locking thumb nut.

On the other hand, if complete disassembly of the thumb nut 828 from the adaptor 820 is desired, the adaptor 820 is oriented in a vertical position (as shown in FIG. 21) and the assembly is simply jiggled by hand until the captivating element 800 aligns itself with the first flange 852 on the adaptor 820. In this aligned position, the flat edge 806 of the captivating element 800 is hidden from the shoulder 831 of the thumb nut 828. It is then a simple matter to unscrew the thumb nut 828 from the adaptor 82 and completely disassemble the thumb nut 828 from the adaptor 820.

Alternatively, the chamfered captivating shoulder could be provided on the adaptor, instead of on the thumb nut. In such a variation of the present invention, the chamfered edge and the flat edge on the captivating element need only be switched to the opposite respective sides of the captivating element.

While the invention has been illustrated with respect to several specific embodiments thereof, these embodiments should be considered a illustrative rather than limiting. Various modifications and additions may be made and will be apparent to those skilled in the art. Accordingly, the invention should not be limited by the foregoing description, but rather should be defined only by the following claims.

What is claimed is:

1. A syringe tip adaptor for connecting a syringe tip to a handpiece body comprising:
    a) a generally cylindrical body having a hollow interior,
    b) a first means for threadably connecting the cylindrical body to the handpiece body,
    c) a baffle mounted within the hollow interior of the cylindrical body and having an axial passageway therein for receiving water from the handpiece body,
    d) means for mounting a syringe tip to the baffle on the interior of the adaptor, the means for mounting comprising an elongated tapered male connector formed integrally with the baffle and having an axial opening therethrough adapted to cooperate with a central passageway in the syringe tip to provide a water passageway from the handpiece through the adaptor and into the syringe tip whereby when the syringe tip is mounted on the tapered male connector, the syringe tip will be tightly held on the tapered male connector to prevent axial rotation of the syringe tip and to ensure that the air and water passageways do not leak into each other, the tapered male connector being of sufficient length to prevent the syringe tip from cracking when it is mounted on the tapered male connector,
    e) at least one channel for introducing air from the handpiece body into the interior of the adaptor and a chamfered surface on the cylindrical body aligned with the channel, f) a first sealing means mounted on the cylindrical body for preventing leakage of water from the handpiece body to the interior of the adaptor, g) a second sealing means mounted on the cylindrical body for preventing the leakage of air passing from the handpiece body to the interior of the adaptor, and h) a third sealing means mounted on the cylindrical body for securing the syringe tip to the interior of the adaptor.

2. The adaptor of claim 1 wherein the first means for connecting is a screw thread.

3. The adaptor of claim 1 wherein the first sealing means is an O ring, and a mounting member is attached to the baffle for securing the O ring to the cylindrical body.

4. The adaptor of claim 1 wherein the second sealing means is an O ring attached to the cylindrical body adjacent the first means for threadably connecting.

5. The adaptor of claim 1 further including second means for connecting the adaptor to a thumb nut.

6. The adaptor of claim 5 wherein the second means for connecting is a screw thread.

7. The adaptor of claim 1 wherein a forward interior portion of the cylindrical body is provided with an hexagonal cross-section for using an allen wrench to connect the adaptor to the handpiece.

8. A syringe tip adaptor for connecting a syringe tip to a handpiece body comprising:

a) a generally cylindrical body having a hollow interior, b) a first means for threadably connecting the cylindrical body to the handpiece body, c) a baffle mounted within the hollow interior of the cylindrical body and having an axial passageway therein for receiving water from the handpiece body, d) means for mounting a syringe tip to the baffle on the interior of the adaptor, e) at least one channel for introducing air from the handpiece body into the interior of the adaptor and a chamfered surface on the cylindrical body aligned with the channel, f) a first sealing means mounted on the cylindrical body for preventing leakage of water from the handpiece body to the interior of the adaptor, g) a second sealing means mounted on the cylindrical body for preventing the leakage of air passing from the handpiece body to the interior of the adaptor, the second sealing means being an O ring attached to the cylindrical body adjacent the first means for threadably connecting, the second sealing means further including a flange member attached to the cylindrical body adjacent the O ring, and h) a third sealing means mounted on the cylindrical body for securing the syringe tip to the interior of the adaptor.

9. A syringe tip adaptor for connecting a syringe tip to a handpiece body comprising:

a) a generally cylindrical body having a hollow interior, b) a first means for threadably connecting the cylindrical body to the handpiece body, c) a baffle mounted within the hollow interior of the cylindrical body and having an axial passageway therein for receiving water from the handpiece body, d) means for mounting a syringe tip to the baffle on the interior of the adaptor, e) at least one channel for introducing air from the handpiece body into the interior of the adaptor and a chamfered surface of the cylindrical body aligned with the channel, f) a first sealing means mounted on the cylindrical body for preventing leakage of water from the handpiece body to the interior of the adaptor, g) a second sealing means mounted on the cylindrical body for preventing the leakage of air passing from the handpiece body to the interior of the adaptor, the second sealing means being an O ring attached to the cylindrical body adjacent the first means for threadably connecting, and h) a third sealing means mounted on the cylindrical body for securing the syringe tip to the interior of the adaptor, the third sealing means comprising an O ring mounted in the forward interior portion of the cylindrical body.

10. A dental syringe assembly comprising a handpiece body and an adaptor for mounting a syringe tip to the handpiece body, said adaptor comprising:

a) a generally cylindrical body having a hollow interior, b) a first means for threadably connecting the cylindrical body to the handpiece body, c) a baffle mounted within the hollow interior of the cylindrical body and having an axial passageway therein for receiving water from the handpiece body, d) means for mounting a syringe tip to the baffle on the interior of the adaptor, the means for mounting comprising an elongated tapered male connector formed integrally with the baffle and having an axial opening therethrough adapted to cooperate with a central passageway in the syringe tip to provide a water passageway from the handpiece through the adaptor and into the syringe tip whereby when the syringe tip is mounted on the tapered male connector, the syringe tip will be tightly held on the tapered male connector to prevent axial rotation of the syringe tip and to ensure that the air and water passageways do not leak into each other, the tapered male connector being of sufficient length to prevent the syringe tip from cracking when it is mounted on the tapered male connector, e) at least one channel for introducing air from the handpiece body into the interior of the adaptor and a chamfered surface on the cylindrical body aligned with the channel, f) a first sealing means mounted on the cylindrical body for preventing leakage of water from the handpiece body to the interior of the adaptor, g) a second sealing means mounted on the cylindrical body for preventing the leakage of air passing from the handpiece body to the interior of the adaptor, and h) a third sealing means mounted on the cylindrical body for securing the syringe tip to the interior of the adaptor.

11. The assembly of claim 10 wherein the first means for connecting is a screw thread.

12. The assembly of claim 10 wherein the first sealing means is an O ring, and a mounting member is attached to the baffle for securing the O ring to the cylindrical body.

13. The assembly of claim 10 wherein the second sealing means is an O ring attached to the cylindrical body adjacent the first means for threadably connecting.

14. The adaptor of claim 10 further including second means for connecting the adaptor to a thumb nut.

15. The adaptor of claim 14 wherein the second means for connecting is a screw thread.

16. The adaptor of claim 10 wherein a forward interior portion of the cylindrical body is provided with an hexagonal cross-section for using an allen wrench to connect the adaptor to the handpiece.

17. A dental syringe assembly comprising a handpiece body and an adaptor for mounting a syringe tip to the handpiece body, said adaptor comprising:
 a) a generally cylindrical body having a hollow interior,
 b) a first means for threadably connecting the cylindrical body to the handpiece body,
 c) a baffle mounted within the hollow interior of the cylindrical body and having an axial passageway therein for receiving water from the handpiece body,
 d) means for mounting a syringe tip to the baffle on the interior of the adaptor,
 e) at least one channel for introducing air from the handpiece body into the interior of the adaptor and a chamfered surface on the cylindrical body aligned with the channel,
 f) a first sealing means mounted on the cylindrical body for preventing leakage of water from the handpiece body to the interior of the adaptor,
 g) a second sealing means mounted on the cylindrical body for preventing the leakage of air passing from the handpiece body to the interior of the adaptor, the second sealing means being an O ring attached to the cylindrical body adjacent the first means for threadably connecting, the second sealing means further including a flange member attached to the cylindrical body adjacent the O ring, and
 h) a third sealing means mounted on the cylindrical body for securing the syringe tip to the interior of the adaptor.

18. A dental syringe assembly comprising a handpiece body and an adaptor for mounting a syringe tip to the handpiece body, said adaptor comprising:
 a) a generally cylindrical body having a hollow interior,
 b) a first means for threadably connecting the cylindrical body to the handpiece body,
 c) a baffle mounted within the hollow interior of the cylindrical body and having an axial passageway therein for receiving water from the handpiece body,
 d) means for mounting a syringe tip to the baffle on the interior of the adaptor,
 e) at least one channel for introducing air from the handpiece body into the interior of the adaptor and a chamfered surface on the cylindrical body aligned with the channel,
 f) a first sealing means mounted on the cylindrical body for preventing leakage of water from the handpiece body to the interior of the adaptor,
 g) a second sealing means mounted on the cylindrical body for preventing the leakage of air passing from the handpiece body to the interior of the adaptor, and
 h) a third sealing means mounted on the cylindrical body for securing the syringe tip to the interior of the adaptor, the third sealing means comprising an O ring mounted in the forward interior portion of the cylindrical body.

19. A dental syringe assembly comprising a handpiece body, a syringe tip and an adaptor for mounting a syringe tip to the handpiece body,
 a) said syringe tip comprising an elongated cylindrical rigid plastic member having a first central water passageway throughout the entire length of the cylindrical member, said first central water passageway being generally circular in cross-section, and a plurality of second air passageways disposed circumferentially about the first central water passageway, said second air passageways extending substantially the entire length of the tip and the combined cross-sectional areas of the second air passageways being at least 30% of the total cross-sectional area that would result if the second air passageways were formed as a single continuous annulus completely surrounding the central water passageway, and
 b) said adaptor comprising:
  1) a generally cylindrical body having a hollow interior,
  2) a first means for threadably connecting the cylindrical body to the handpiece body,
  3) a baffle mounted within the hollow interior of the cylindrical body and having an axial passageway therein for receiving water from the handpiece body,
  4) means for mounting a syringe tip to the baffle on the interior of the adaptor, the means for mounting comprising an elongated tapered male connector formed integrally with the baffle and having an axial opening therethrough adapted to cooperate with a central passageway in the syringe tip to provide a water passageway from the handpiece through the adaptor and into the syringe tip whereby when the syringe tip is mounted on the tapered male connector, the syringe tip will be tightly held on the tapered male connector to prevent axial rotation of the syringe tip and to ensure that the air and water passageways do not leak into each other, the tapered male connector being of sufficient length to prevent the syringe tip from cracking when it is mounted on the tapered male connector,
  5) at least one channel for introducing air from the handpiece body into the interior of the adaptor and a chamfered surface on the cylindrical body aligned with the channel,
  6) at first sealing means mounted on the cylindrical body for preventing leakage of water from the handpiece body to the interior of the adaptor,
  7) a second sealing means mounted on the cylindrical body for preventing the leakage of air passing from the handpiece body to the interior of the adaptor, and
  8) a third sealing means mounted on the cylindrical body for securing the syringe tip to the interior of the adaptor.

20. The syringe tip of claim 19 wherein there are six second passageways, each second passageway is generally circular and has a diameter in a range of generally 0.021"–0.024".

21. The syringe tip of claim 20 wherein each second passageway has a diameter of approximately 0.022".

22. The syringe tip of claim 19 wherein there are six second passageways and each second passageway is elliptical in shape and arranged radially to the central passageway.

23. The syringe tip of claim wherein there are six second passageways and each second passageway is elliptical in shape and arranged tangentially to the central passageway.

24. A thumb nut assembly securing an externally threaded syringe tip adaptor to an internally threaded thumb nut comprising:
   (a) a generally flat washer-like captivating element having a generally circular cross-section with a portion of its circumference omitted, a first side of the captivating element having a beveled edge around its entire circumference and a second side of the captivating element having a flat edge around its entire circumference, and
   (b) means for positioning the captivating element between the adaptor and the thumb nut whereby when the thumb nut is threaded onto the adaptor, the captivating element aligns itself along the axis of the adaptor to allow the thumb nut to receive the adaptor; and when the thumb nut is unthreaded from the adaptor, the captivating element prevents disassembly unless the adaptor and the thumb nut are positioned in a particular orientation.

25. A thumb nut assembly securing an externally threaded first member to an internally threaded second member comprising:
   a) the externally threaded first member including a generally cylindrical body having a threaded exterior and a recessed portion defined by a first flange member and a second flange member for receiving a captivating element,
   b) the internally threaded second member including a shoulder portion at one end, said shoulder portion having on one side a beveled edge around its entire circumference and on the other side a flat edge around its entire circumference, and
   c) the captivating element mounted in the recessed portion of the first member comprising a generally flat washer-like member having a generally circular cross-section with a portion of its circumference omitted, a first side of the washer-like member having a beveled edge around its entire circumference and a second side of the washer-like member having a flat edge around its entire circumference, the internal cross-section of the captivating element being larger than the external cross-section of the recessed portion of the externally-threaded first member so that the captivating element hangs loosely about the externally-threaded first member,
   whereby when the second member is threaded onto the first member, the captivating element aligns itself along the axis of the first member to allow the second member to receive the first member; and when the second member is unthreaded from the first element, the captivating element prevents disassembly unless the first and second members are positioned in a particular orientation.

26. A syringe tip assembly for mounting a syringe tip to a handpiece body comprising:
   a) an adaptor having external threads and including means for mounting a syringe tip to the adaptor, and
   b) an internally threaded thumb nut assembly for securing the syringe tip to the adaptor comprising:
      1) the adaptor member including a generally cylindrical body having a threaded exterior and a recessed portion defined by a first flange member and a second flange member for receiving a captivating element,
      2) the thumb nut including a shoulder portion at one end, said shoulder portion having on one side and a beveled edge around its entire circumference and on the other side a flat edge around its entire circumference, and
      3) a captivating element mounted in the recessed portion of the adaptor, said captivating element comprising a generally flat washer-like member having a generally circular cross-section with a portion of its circumference omitted, a first side of the washer-like member having a beveled edge around its entire circumference and a second side of the washer-like member having a flat edge around its entire circumference, the internal cross-section of the captivating element being larger than the external cross-section of the recessed portion of the adaptor so that the captivating element hangs loosely about the adaptor,
   whereby when the thumb nut is threaded onto the adaptor, the captivating element aligns itself along the axis of the adaptor to allow the thumb nut to receive the adaptor; and when the thumb nut is unthreaded from the adaptor, the captivating element prevents disassembly unless the adaptor and the thumb nut are positioned in a particular orientation.

27. A dental syringe assembly comprising a handpiece body, a syringe tip, an adaptor for mounting a syringe tip to the handpiece body and a captivating thumb nut assembly for securing the syringe tip to the adaptor,
   a) said syringe tip comprising an elongated cylindrical rigid plastic member having a first central water passageway throughout the entire length of the cylindrical member, said first central water passageway being generally circular in cross-section, and a plurality of second air passageways disposed circumferentially about the first central water passageway, said second air passageways extending substantially the entire length of the tip and the combined cross-sectional areas of the second air passageways being at least 30% of the total cross-sectional area that would result if the second air passageways were formed as a single continuous annulus completely surrounding the central water passageway,
   b) said adaptor comprising:
      1) a generally cylindrical body having a hollow interior,
      2) a first means for connecting the cylindrical body to the handpiece body,
      3) a baffle mounted within the hollow interior of the cylindrical body and having an axial passageway therein for receiving water from the handpiece body,
      4) means for mounting a syringe tip to the baffle on the interior of the adaptor,
      5) at least one channel for introducing air from the handpiece body into the interior of the adaptor and a chamfered surface on the cylindrical body aligned with the channel, 6) a first sealing means mounted on the cylindrical body for preventing leakage of water from the handpiece body to the interior of the adaptor, 7) a second sealing means mounted on the cylindrical body for preventing leakage of air from the handpiece body to the interior of the adaptor, and 8) a third sealing means mounted on the cylindrical body for securing the syringe tip to the interior of the adaptor, and c) said thumb nut assembly comprising:

1) the adaptor member including a generally cylindrical body having a threaded exterior and a recessed portion defined by a first flange member and a second flange member for receiving a captivating element, 2) an internally threaded thumb nut including a shoulder portion at one end, said shoulder portion having on one side a beveled edge around its entire circumference and on the other side a flat edge around its entire circumference, and 3) a captivating element mounted in the recessed portion of the adaptor, said captivating element comprising a generally flat washer-like member having a generally circular cross-section with a portion of its circumference omitted, a first side of the washer-like member having a beveled edge around its entire circumference and a second side of the washer-like member having a flat edge around its entire circumference, the internal cross-section of the captivating element being larger than the external cross-section of the recessed portion of the adaptor so that the captivating element hangs loosely about the adaptor, whereby when the thumb nut is threaded onto the adaptor, the captivating element aligns itself along the axis of the adaptor to allow the thumb nut to receive the adaptor; and when the thumb nut is unthreaded from the adaptor, the captivating element prevents disassembly unless the adaptor and the thumb nut are positioned in a particular orientation.

28. The adaptor of claim 27 wherein the means for mounting is a tapered male connector formed integrally with the baffle and having an axial opening therethrough, the tapered male connector being of sufficient length to prevent the syringe tip from cracking when it is mounted on the male connector.

29. The syringe tip of claim 27 wherein there are six second passageways, each second passageway is generally circular and has a diameter in a range of generally 0.021"–0.024".

30. The syringe tip of claim 29 wherein each second passageway has a diameter of approximately 0.022".

31. The syringe tip of claim 27 wherein there are six second passageways and each second passageway elliptical in shape and arranged radially to the central passageway.

32. The syringe tip of claim 27 wherein there are six second passageways and each second passageway is elliptical in shape and arranged tangentially to the central passageway.

* * * * *